(12) United States Patent
Zhu

(10) Patent No.: US 9,883,698 B2
(45) Date of Patent: Feb. 6, 2018

(54) REPLACEABLE VAPORIZER ASSEMBLY AND ELECTRONIC CIGARETTE HAVING THE SAME

(71) Applicant: Xiaochun Zhu, Shenzhen (CN)

(72) Inventor: Xiaochun Zhu, Shenzhen (CN)

(73) Assignee: Shenzhen Kanger Technologies Co., Ltd., Shenzhen (CN)

( * ) Notice: Subject to any disclaimer, the term of this patent is extended or adjusted under 35 U.S.C. 154(b) by 5 days.

(21) Appl. No.: 15/203,793

(22) Filed: Jul. 7, 2016

(65) Prior Publication Data

US 2018/0007963 A1 Jan. 11, 2018

(51) Int. Cl.
*A24F 47/00* (2006.01)
*H05B 3/42* (2006.01)

(52) U.S. Cl.
CPC ............. *A24F 47/008* (2013.01); *H05B 3/42* (2013.01); *H05B 2203/021* (2013.01)

(58) Field of Classification Search
None
See application file for complete search history.

(56) References Cited

U.S. PATENT DOCUMENTS

| 9,078,474 | B2 * | 7/2015 | Thompson | ............ | A24F 47/008 |
| 9,101,729 | B2 * | 8/2015 | Liu | ........ | A61M 15/06 |
| 2016/0295923 | A1 * | 10/2016 | Lin | ........ | A24F 47/008 |
| 2017/0086506 | A1 * | 3/2017 | Rado | .................... | H05B 1/0227 |

\* cited by examiner

*Primary Examiner* — Tho D Ta
(74) *Attorney, Agent, or Firm* — Ming Jiang; MM IP Services LLC

(57) ABSTRACT

The present disclosure relates to a replaceable vaporizer assembly and an electronic cigarette having the replaceable vaporizer assembly. In certain embodiments, the electronic cigarette may include an electronic cigarette body, and a replaceable vaporizer assembly. The electronic cigarette body may include a mouthpiece installed in a mouthpiece base, a connector base, a mounting base, an E-liquid storage tank, and a connector. The mounting base and the connector base are threadedly connected through a first internal thread of the mounting base and an external thread of the connector base to form an air chamber inside of the mounting base and the connector base. When in operation, outside air enters the air chamber through the multiple air intake openings and is vaporized by the replaceable vaporizer assembly, goes up through multiple air gaps between the mounting base and the connector base, and exits the electronic cigarette body through the mouthpiece.

19 Claims, 10 Drawing Sheets

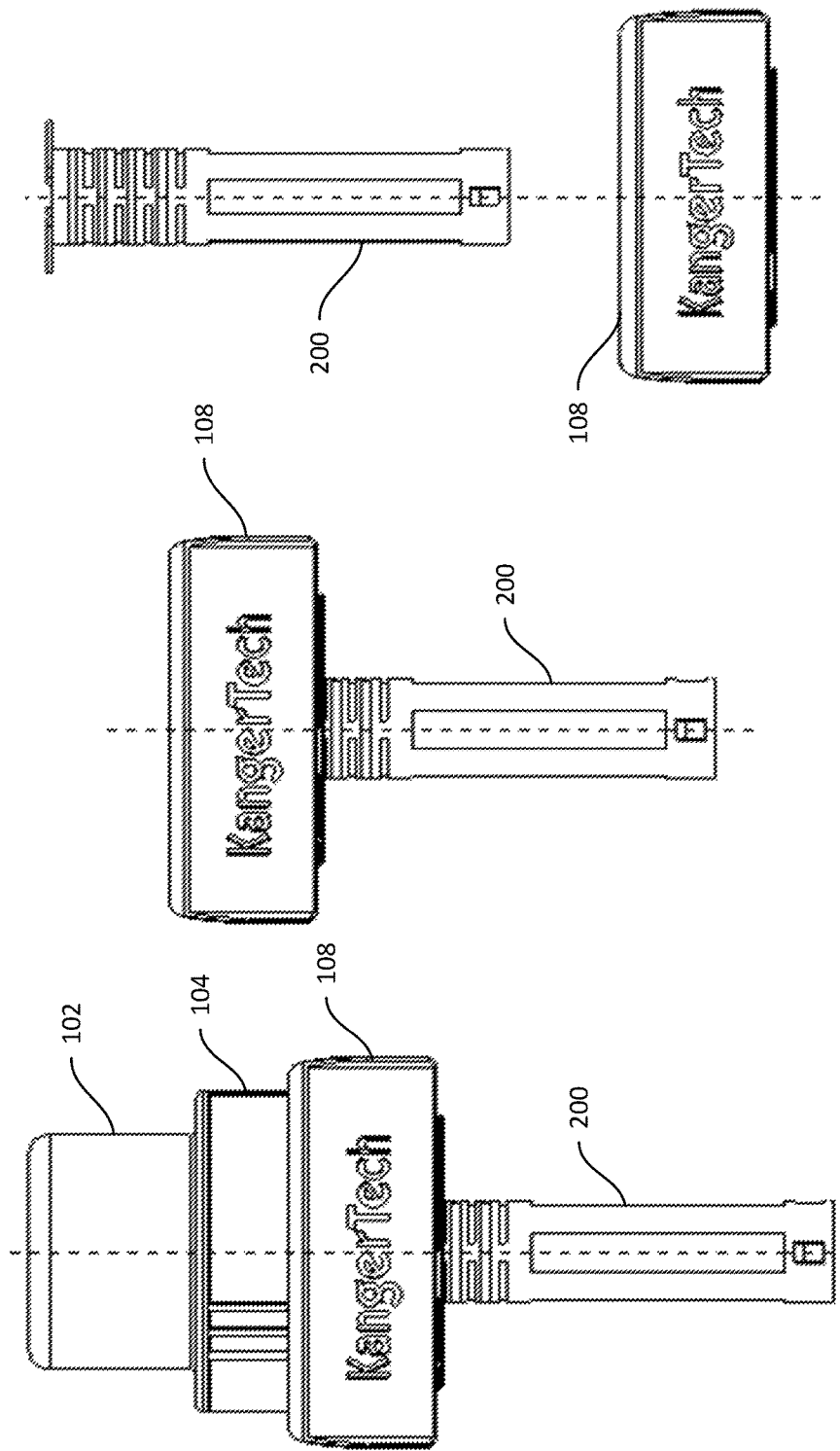

REPLACEABLE VAPORIZER ASSEMBLY AND ELECTRONIC CIGARETTE HAVING THE SAME

FIELD

The present disclosure generally relates to the field of electronic cigarette, and more particularly to replaceable vaporizer assemblies and electronic cigarettes having the replaceable vaporizer assemblies.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

It is well known that smoking cigarette is harmful to smoker's health. The active ingredient in a cigarette is mainly nicotine. During smoking, nicotine, along with tar aerosol droplets produced in the cigarette burning, are breathed into the alveolus and absorbed quickly by the smoker. Once nicotine is absorbed into the blood of the smoker, nicotine then produces its effect on the receptors of the smoker's central nervous system, causing the smoker relax and enjoy an inebriety similar to that produced by an exhilarant.

The electronic cigarette is sometimes referred as electronic vaporing device, personal vaporizer (PV), or electronic nicotine delivery system (ENDS). It is a battery-powered device which simulates tobacco smoking. It generally uses a heating element that vaporizes a liquid solution (e-liquid). Some solutions contain a mixture of nicotine and a variety of flavorings, while others release a flavored vapor without nicotine. Many are designed to simulate smoking experience, such as cigarette smoking or cigar smoking. Some of them are made with similar appearance, while others are made considerably different in appearance.

Replacing a vaporizer in a conventional electronic cigarette is difficult. When E-liquid gets on the vaporizer while someone is replacing the vaporizer, he/she may be contaminated with E-liquid, and it is hard to clean. Therefore, it is desirable to replace the vaporizer easily without getting E-liquid contamination.

Therefore, an unaddressed need exists in the art to address the aforementioned deficiencies and inadequacies.

SUMMARY

In one aspect, the present disclosure relates to a replaceable vaporizer assembly. In certain embodiments, the replaceable vaporizer assembly may include an E-liquid storage medium, and a heating element. The heating element may include a positive terminal, and a negative terminal. The positive terminal is electrically coupled to a positive terminal of a power module, and the negative terminal is electrically coupled to a negative terminal of the power module. When the power module is switched on, the heating element is energized by the power module to heat E-liquid stored in the E-liquid storage medium from an E-liquid storage tank to produce E-liquid vapor for an electronic cigarette.

In another aspect, the present disclosure relates to an electronic cigarette body 100. The electronic cigarette body may include: a mouthpiece, a mouthpiece base, a connector base, a mounting base, an E-liquid storage tank, and a connector. In certain embodiments, the mouthpiece base may define a center opening to slidedly fit the mouthpiece. The mouthpiece base may include an external thread.

In certain embodiments, the electronic cigarette body may install a replaceable vaporizer assembly. The replaceable vaporizer assembly may include an E-liquid storage medium and a heating element. In certain embodiments, the heating element may have a positive terminal and a negative terminal. The positive terminal is electrically coupled to a positive terminal of the power module, and the negative terminal is electrically coupled to a negative terminal of the power module, when the power module is switched on the heating element is energized by the power module to heat E-liquid stored in the E-liquid storage medium from an E-liquid storage tank to produce E-liquid vapor for an electronic cigarette.

In yet another aspect, the present disclosure relates to an electronic cigarette. In certain embodiments, the electronic cigarette may include an electronic cigarette body, and a replaceable vaporizer assembly. The electronic cigarette body may include a mouthpiece installed in a mouthpiece base, a connector base, a mounting base, an E-liquid storage tank, and a connector. The mounting base and the connector base are threadedly connected through a first internal thread of the mounting base and an external thread of the connector base to form an air chamber inside of the mounting base and the connector base. When in operation, outside air enters the air chamber through the multiple air intake openings and is vaporized by the replaceable vaporizer assembly, goes up through multiple air gaps between the mounting base and the connector base, and exits the electronic cigarette body through the mouthpiece.

These and other aspects of the present disclosure will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the disclosure and, together with the written description, serve to explain the principles of the disclosure. Wherever possible, the same reference numbers are used throughout the drawings to refer to the same or like elements of an embodiment. The drawings do not limit the present disclosure to the specific embodiments disclosed and described herein. The drawings are not necessarily to scale, emphasis instead being placed upon clearly illustrating the principles of the disclosure, and wherein:

FIG. 9A shows an external view of the electronic cigarette having the mouthpiece, the mouthpiece base, the connector based and the replaceable vaporizer assembly removed from the electronic cigarette for replacing the replaceable vaporizer assembly, FIG. 9B shows an external view of the electronic cigarette having the replaceable vaporizer assembly attached to the connector base, and FIG. 9C shows the replaceable vaporizer assembly has been removed from the top of the connector base according to certain embodiments of the present disclosure.

DETAILED DESCRIPTION

Figure 1:
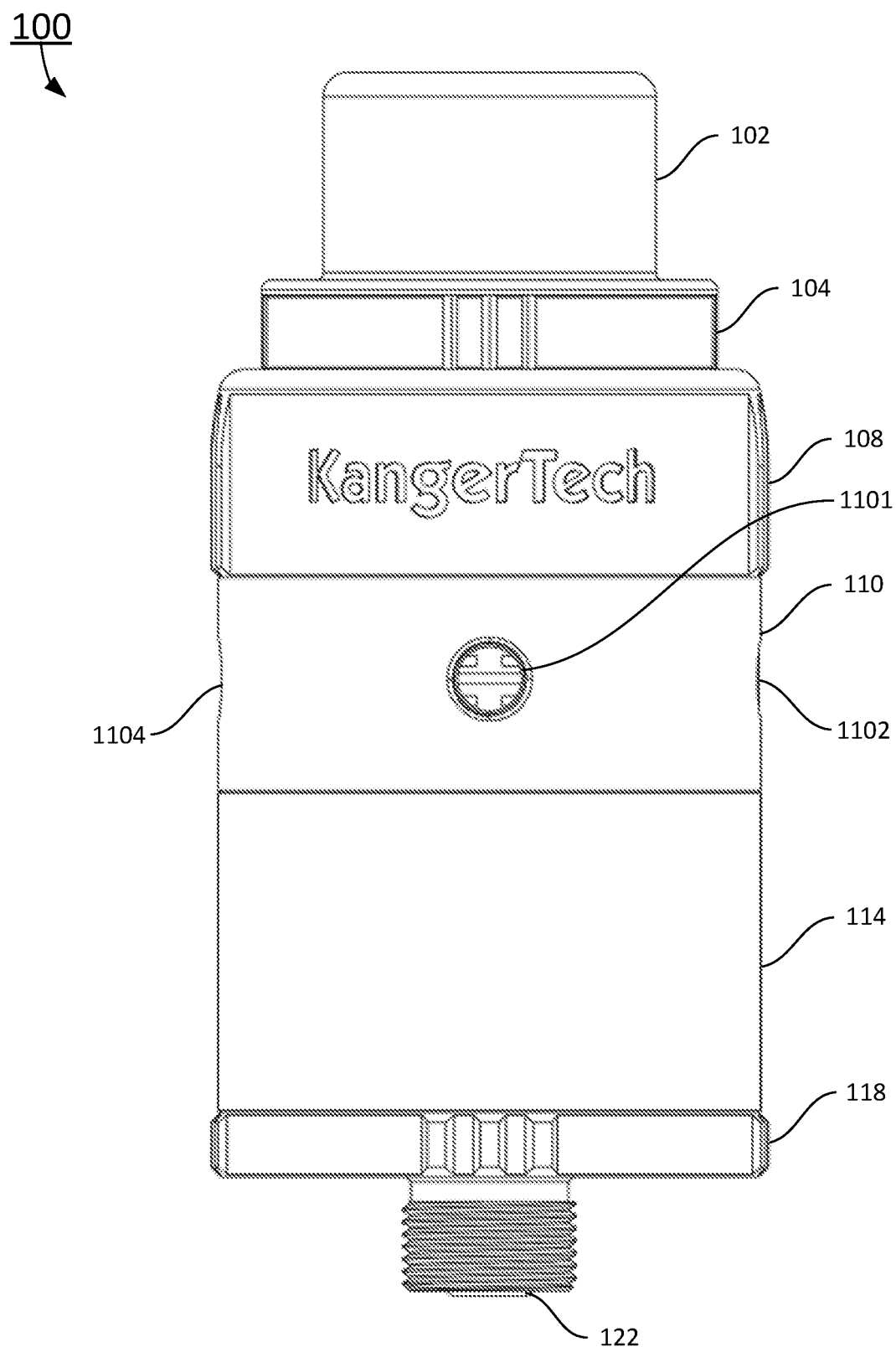
FIG. 1 is an external view of an exemplary electronic cigarette having a replaceable vaporizer assembly according to certain embodiments of the present disclosure.

The present disclosure will now be described more fully hereinafter with reference to the accompanying drawings, in which exemplary embodiments of the disclosure are shown. This disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom", "upper" or "top," and "front" or "back" may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximates, meaning that the term "around", "about" or "approximately" can be inferred if not expressly stated.

Many specific details are provided in the following descriptions to make the present disclosure be fully understood, but the present disclosure may also be implemented by using other manners different from those described herein, so that the present disclosure is not limited by the specific embodiments disclosed in the following.

The description will be made as to the embodiments of the present disclosure in conjunction with the accompanying drawings FIGS. 1 through 10.

Referring now to FIG. 1, an external view of an exemplary electronic cigarette 100 is shown according to certain embodiments of the present disclosure. The electronic cigarette 100 includes multiple distinctive features of present disclosure: an easy replaceable vaporizer assembly, an easy E-liquid refilling mechanism, and a new air flow mechanism for the electronic cigarette 100. In certain embodiments, the electronic cigarette 100 may include: a mouthpiece 102, a mouthpiece base 104, a connector base 108, a mounting base 110, an E-liquid storage tank 114, and a connector 118.

In certain embodiments, the mouthpiece 102 may be removed from the mouthpiece base 104 by pulling the mouthpiece 102 upwards. A sealing ring 1021 (not shown in FIG. 1) of the mouthpiece 102 may be used to snuggly fit the mouthpiece 102 into the mouthpiece base 104. The mouthpiece base 104 and the connector base 108 may be threadedly connected together. The connector base 108 and the mounting base 110 may be threadedly connected together. The mounting base 110 and the connector 118 may be threadedly connected to form the E-liquid storage tank 114.

In certain embodiments, the mounting base 110 may define multiple air intake openings 1101, 1102, . . . , 110N, where N is a positive integer. These air intake openings are evenly distributed along the perimeters of the mounting base 110 to provide air into an air chamber 150 (not shown in FIG. 1) inside the mounting base 110. As shown in FIG. 1, the mounting base 110 defined four air intake openings: a first air intake opening 1101, a second air intake opening 1102, a third air intake opening 1103 (not shown in FIG. 1), and a fourth air intake opening 1104. These multiple air intake openings forms the air flow mechanism for the electronic cigarette 100. Unlike conventional air intakes are located near the bottom of the electronic cigarette 100, these air intake openings are located near the top of the electronic cigarette 100. The vaporization occurs near the top of the electronic cigarette 100 such that any water vapor may flow to the bottom and will not get into user's mouth through the mouthpiece 102.

In certain embodiments, the electronic cigarette 100 may include a positive terminal 122, and a negative terminal form by the connector 118. The connector 118 may include a second external thread 118 configured to threadedly connect to an internal thread of a power module (not shown in FIG. 1).

Figure 2:
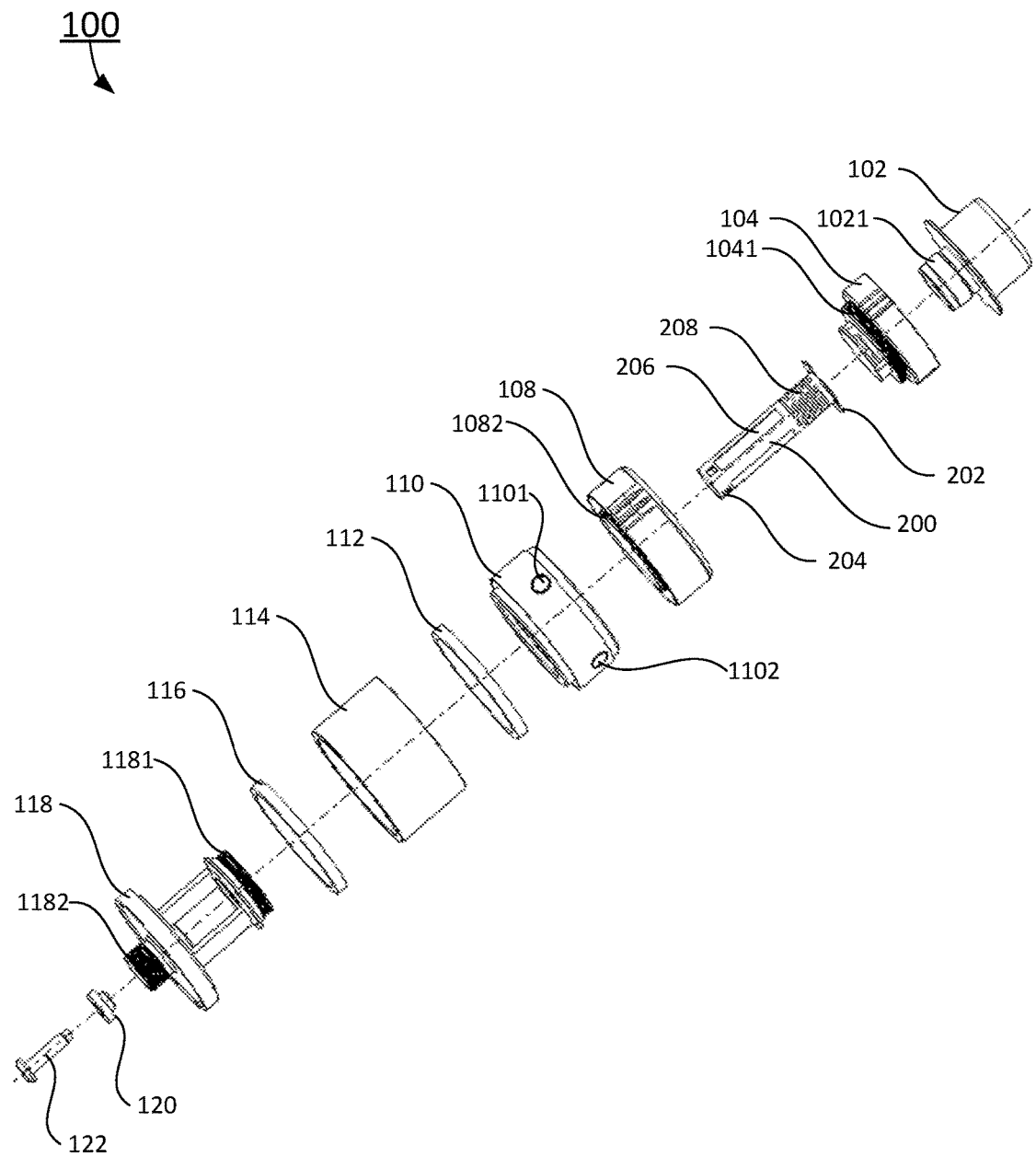
FIG. 2 is an exploded perspective view of the electronic cigarette having the replaceable vaporizer assembly according to certain embodiments of the present disclosure.
Figure 3:
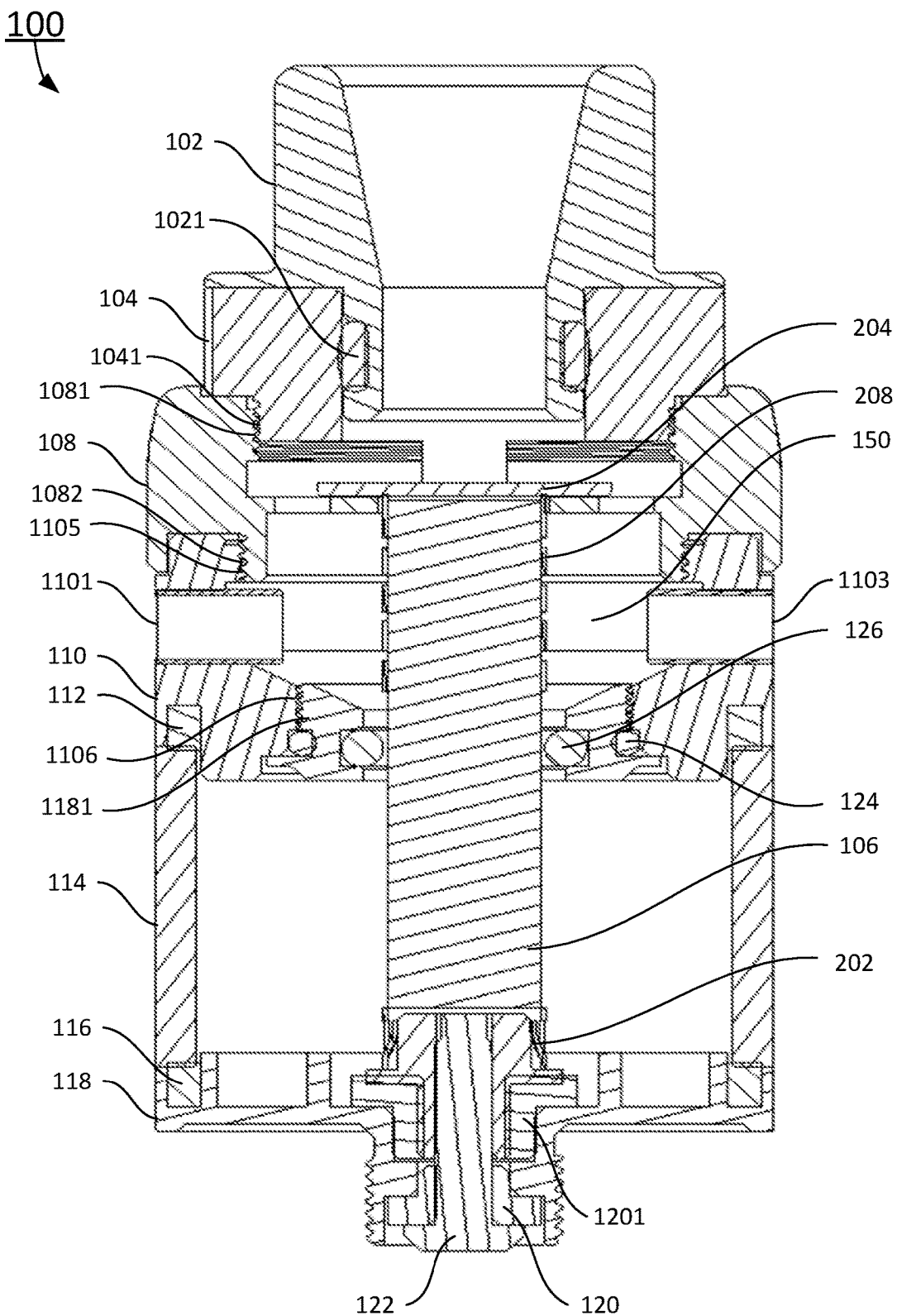
FIG. 3 is a detailed cross-sectional view of the electronic cigarette having the replaceable vaporizer assembly according to certain embodiments of the present disclosure.

Referring now to FIGS. 2 and 3, an exploded perspective view of the electronic cigarette 100 having a replaceable vaporizer assembly 200 and a detailed cross-sectional view of the electronic cigarette 100 are shown according to certain embodiments of the present disclosure.

In one aspect, the present disclosure relates to a replaceable vaporizer assembly 200. In certain embodiments, the replaceable vaporizer assembly 200 may include an E-liquid storage medium 206, and a heating element 208. The heating element 208 may include a positive terminal 202, and a negative terminal 204. The positive terminal 202 is electrically coupled to a positive terminal of the power module, and the negative terminal 204 is electrically coupled to a negative terminal of the power module. When the power module is switched on, the heating element 208 is energized by the power module to heat E-liquid stored in the E-liquid storage medium 206 from an E-liquid storage tank 114 to produce E-liquid vapor for an electronic cigarette.

In certain embodiments, the E-liquid storage medium 206 may include: a cylindrical E-liquid storage medium 206 and a round E-liquid storage medium 206. In one embodiment, the cylindrical E-liquid storage medium 206 may be installed outside of the heating element 208. In another embodiment, the round E-liquid storage medium 206 may be installed inside of the heating element 208. In certain embodiments, the E-liquid storage medium 206 may include: cotton fibers, polypropylene fibers, terylene fibers, nylon fibers, porous ceramic materials, or any combinations of these materials.

In certain embodiments, the heating element 208 may be formed on a cylindrical tube having a top portion, a middle portion and a bottom portion. The heating element 208 may be formed at the top portion, the middle portion, or the bottom portion of the cylindrical tube.

In certain embodiments, the heating element 208 may include multiple heating elements to increase amount of E-liquid vapor generated. In one embodiment, these heating elements may be electrically coupled in serial. In another embodiment, these heating elements may be electrically coupled in parallel. In certain embodiments, these heating elements may be formed at the top portion, the middle portion, and/or the bottom portion of the cylindrical tube.

In certain embodiments, the heating element 208 is made of resistive electrical conductive materials having large contact area with the E-liquid storage medium 206 to increase amount of E-liquid vapor generated. In certain embodiments, the heating element 208 may include: a grid shaped heating element, a mesh shaped heating element, a net shaped heating element, a spiral heating element, and any combinations of these shapes.

In another aspect, the present disclosure relates to an electronic cigarette body 100. The electronic cigarette body 100 may include: a mouthpiece 102, a mouthpiece base 104, a connector base 108, a mounting base 110, an E-liquid storage tank 114, and a connector 118. In certain embodiments, the mouthpiece base 104 may define a center opening to slidedly fit the mouthpiece 102. A sealing ring 1021 of the mouthpiece 102 may be used to ascertain reliable connection between the mouthpiece 102 and the mouthpiece base 104. The mouthpiece base 104 may include an external thread 1041.

In certain embodiments, the connector base 108 may include an internal thread 1081 and an external thread 1082. The internal thread 1081 may threadedly connect to the external thread 1041 of the mouthpiece base 104.

In certain embodiments, the mounting base 110 may define multiple air intake openings 1101, 1102, . . . , 110N, where N is a positive integer. These air intake openings are evenly distributed along the perimeters of the mounting base 110 to provide air into an air chamber 150 (not shown in FIGS. 2 and 3) inside the mounting base 110. As shown in FIG. 1, the mounting base 110 defined four air intake openings: a first air intake opening 1101, a second air intake opening 1102, a third air intake opening 1103 (as shown in FIG. 3), and a fourth air intake opening 1104 (not shown in FIGS. 2 and 3). These multiple air intake openings forms the air flow mechanism for the electronic cigarette body 100. Unlike conventional air intakes are located near the bottom of the electronic cigarette body 100, these air intake openings are located near the top of the electronic cigarette body 100. The vaporization occurs near the top of the electronic cigarette body 100 such that any water vapor may flow to the bottom and will not get into user's mouth through the mouthpiece 102.

Figure 4:
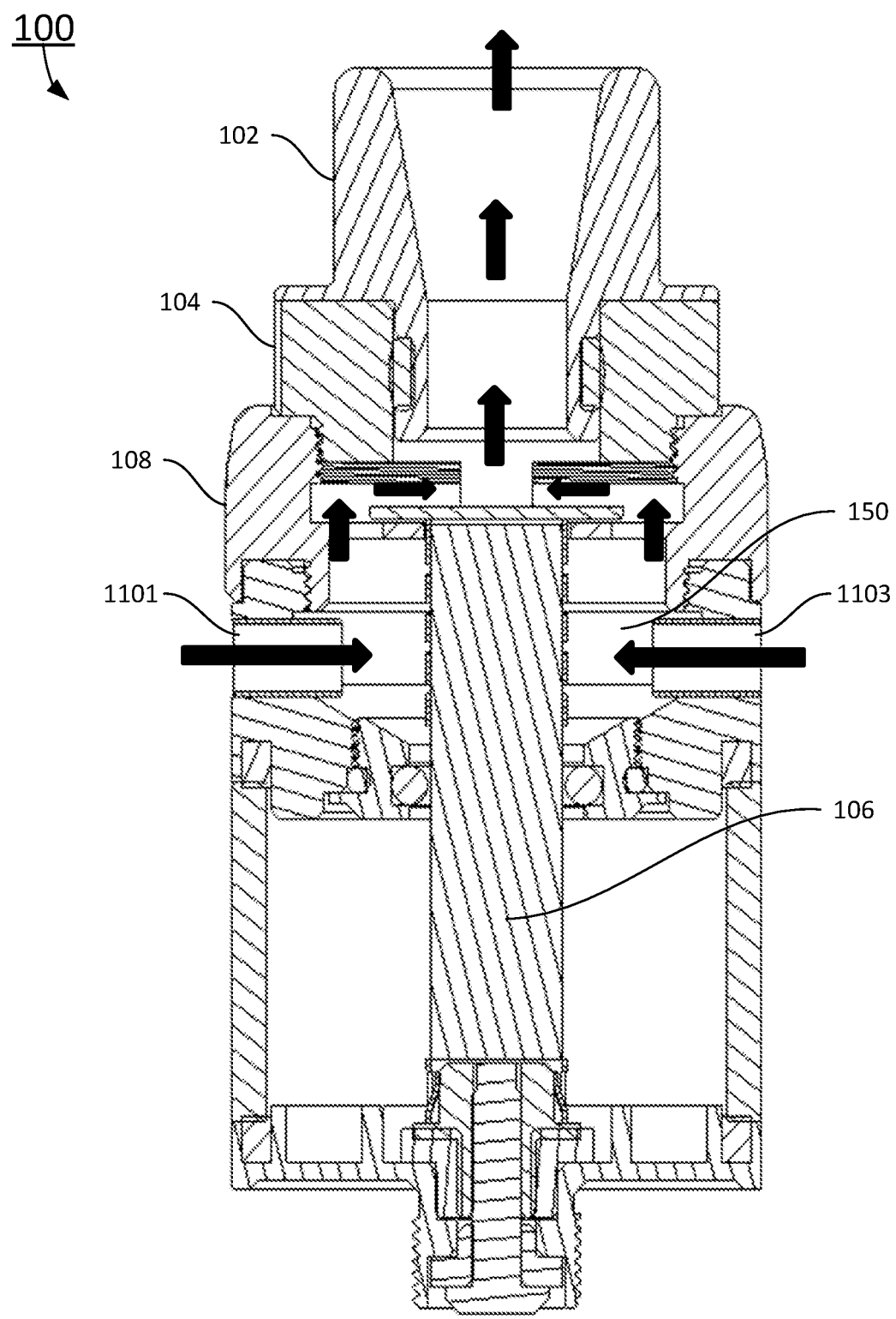
FIG. 4 is a detailed cross-sectional view of an air passage of the electronic cigarette showing air flow according to certain embodiments of the present disclosure.

These air intake openings are evenly distributed along the perimeters of the mounting base 110 to provide air into an air chamber 150 (as shown in FIG. 4) inside the mounting base 110. The mounting base 110 may include a first internal thread 1105 and a second internal thread 1106. The first internal thread 1105 may threadedly connect to the external thread 1082 of the connector base 108.

In certain embodiments, the E-liquid storage tank 114 may have a top end and a bottom end. The E-liquid storage tank 114 is positioned between the mounting base 110 and the connector 118. The E-liquid storage tank 114 may be sealed by a first sealing ring 112 between the mounting base 110 on the top end of the E-liquid storage tank 114 and a second sealing ring 116 between the bottom end of the E-liquid storage tank 114 and the connector 118. The E-liquid in the E-liquid storage tank 114 is in communication with the E-liquid storage medium 206.

In certain embodiments, the connector 118 may include a first external thread 1181 configured to threadedly connect to the second internal thread of the mounting base 110, and a second external thread 1182 configured to threadedly connect to a negative terminal of a power module.

In certain embodiments, the electronic cigarette body 100 may install a replaceable vaporizer assembly 200. The replaceable vaporizer assembly 200 may include an E-liquid storage medium 206 and a heating element 208. In certain embodiments, the heating element 208 may have a positive terminal 202 and a negative terminal 204. The positive terminal 202 is electrically coupled to a positive terminal of the power module, and the negative terminal 204 is electrically coupled to a negative terminal of the power module, when the power module is switched on the heating element 208 is energized by the power module to heat E-liquid stored in the E-liquid storage medium 206 from an E-liquid storage tank 114 to produce E-liquid vapor for an electronic cigarette.

In certain embodiments, the electronic cigarette body 100 may include a positive terminal 122 of the replaceable vaporizer assembly 200 and an insulation tube 120. The positive terminal 122 of the replaceable vaporizer assembly 200 may be electrically coupled to the positive terminal 202 of the heating element 208 and the positive terminal of the power module. The insulation tube 120 may be used to insulate the positive terminal 122 of the replaceable vaporizer assembly 200 and the second external thread 1182 of the connector 118. The second external thread 1182 of the connector 118 forms a negative terminal of the replaceable vaporizer assembly 200.

In certain embodiments, the mounting base 110 and the connector base 108 are threadedly connected through the first internal thread 1105 of the mounting base 110 and the external thread 1082 of the connector base 108 to form an air chamber 150 inside of the mounting base 110 and the connector base 108. Outside air enters the air chamber 150 to be vaporized by the replaceable vaporizer assembly 200 through the multiple air intake openings, goes up through multiple gaps between the mounting base 110 and the connector base 108, and exits the electronic cigarette body 100 through the mouthpiece 102.

In yet another aspect, the present disclosure relates to an electronic cigarette. In certain embodiments, the electronic cigarette may include an electronic cigarette body 100, and a replaceable vaporizer assembly 200. The electronic cigarette body 100 may include a mouthpiece 102 installed in a mouthpiece base 104, a connector base 108, a mounting base 110, an E-liquid storage tank 114, and a connector 118.

In certain embodiments, the connector base 108 may include an internal thread 1081 and the external thread 1082. The internal thread 1081 may threadedly connect to an external thread 1041 of the mouthpiece base 104. The mounting base 110 may include the first internal thread 1105 and a second internal thread 1106. The first internal thread 1105 may threadedly connect to the external thread 1082 of the connector base 108. The connector 118 may include a first external thread 1181 and a second external thread 1182. The first external thread 1181 may threadedly connect to the second internal thread 1106 of the mounting base 110. The second external thread 1182 forms a negative terminal of the electronic cigarette body 100, and may be threadedly connect to an internal thread of a power module.

In certain embodiments, the electronic cigarette body 100 may also include: a positive terminal 122 of the electronic cigarette body 100, and an insulation tube 120. The positive terminal 122 of the electronic cigarette body 100 may be electrically coupled to the positive terminal of a heating element 208 and the positive terminal of the power module. The insulation tube 120 may insulate the positive terminal 122 of the electronic cigarette body 100 and the second external thread 1182 of the connector 118. The second external thread 1182 of the connector 118 forms a negative terminal of the electronic cigarette body 100.

In certain embodiments, the E-liquid storage tank 114 is positioned between the mounting base 110 and the connector 118. The E-liquid storage tank 114 is sealed by a first sealing ring 112 between the mounting base 110 on a top end of the E-liquid storage tank 114 and a second sealing ring 116 between a bottom end of the E-liquid storage tank 114 and the connector 118. E-liquid in the E-liquid storage tank 114 is in communication with the E-liquid storage medium.

In certain embodiments, a third sealing ring 124 is used between the air chamber 150 and the E-liquid storage tank 114 to prevent the E-liquid in the E-liquid storage tank 114 from getting into the air chamber 150, and prevent the air/vapor in the air chamber 150 from getting into the E-liquid storage tank 114. A fourth sealing ring 126 may be used between the replaceable vaporizer assembly 200 and the connector 118. The fourth sealing ring 126 is not tightly sealing the gap between the replaceable vaporizer assembly 200 and the connector 118. Certain air gaps may exist such that the E-liquid storage tank 114 may have normal air pressure allowing the E-liquid in the E-liquid storage tank 114 to be in communication freely with the E-liquid storage medium 206 and provide the E-liquid storage medium 206 with the E-liquid.

In certain embodiments, the replaceable vaporizer assembly 200 may include: an E-liquid storage medium 206, and the heating element 208. The heating element 208 may have a positive terminal 202, and a negative terminal 204. The positive terminal 202 is electrically coupled to a positive terminal of the power module, and the negative terminal is electrically coupled to a negative terminal of the power module, when the power module is switched on the heating element is energized by the power module to heat E-liquid stored in the E-liquid storage medium from the E-liquid storage tank to produce E-liquid vapor for the electronic cigarette.

In certain embodiments, the heating element 208 may include multiple heating elements to increase amount of E-liquid vapor generated. In one embodiment, the multiple heating elements may be electrically coupled in serial. In another embodiment, the multiple heating elements may be electrically coupled in parallel.

In certain embodiments, the heating element 208 is made of resistive electrical conductive materials having large contact area with the E-liquid storage medium 206 to increase amount of E-liquid vapor generated. In certain embodiments, the heating element 208 may include: a grid shaped heating element, a mesh shaped heating element, a net shaped heating element, a spiral heating element, and any combinations of these shapes.

In certain embodiments, the E-liquid storage medium may include a cylindrical E-liquid storage medium 206 and a round E-liquid storage medium 206. The cylindrical E-liquid storage medium 206 may be installed outside of the heating element 208. The round E-liquid storage medium 206 may be installed inside of the heating element 208. In certain embodiments, the E-liquid storage medium 206 may include cotton fibers, polypropylene fibers, terylene fibers, nylon fibers, porous ceramic materials, and any combination of these materials.

Referring now to FIG. 4, a detailed cross-sectional view of an air passage of the electronic cigarette 100 is shown according to certain embodiments of the present disclosure. In certain embodiments, the mounting base 110 may define multiple air intake openings 1101, 1102, . . . , 110N, where N is a positive integer. The mounting base 110 and the connector base 108 are threadedly connected through a first internal thread 1105 of the mounting base 110 and an external thread 1082 of the connector base 108 to form an air chamber 150 inside of the mounting base 110 and the connector base 108. When in operation, outside air enters the air chamber 150 through the multiple air intake openings and is vaporized by the replaceable vaporizer assembly 200, goes up through multiple air gaps between the mounting base 110 and the connector base 108, and exits the electronic cigarette body 100 through the mouthpiece 102.

In certain embodiments, the air passage is marked by a series of arrows. Air outside of the electronic cigarette body 100 enters the electronic cigarette body 100 through the first air intake opening 1101, the second air intake opening 1102, the third air intake opening 1103, and the fourth air intake opening 1104 of the mounting base 110 into the air chamber 150. The air in the air chamber 150 is vaporized by the replaceable vaporizer assembly 200 to form E-liquid vapor, and then the E-liquid vapor goes up through multiple air gaps of the connector base 108 and then continues to move to the center of the connector base 108 and upwards to the mouthpiece 102 due to a vacuum formed by sucking action of a user.

Figure 5:
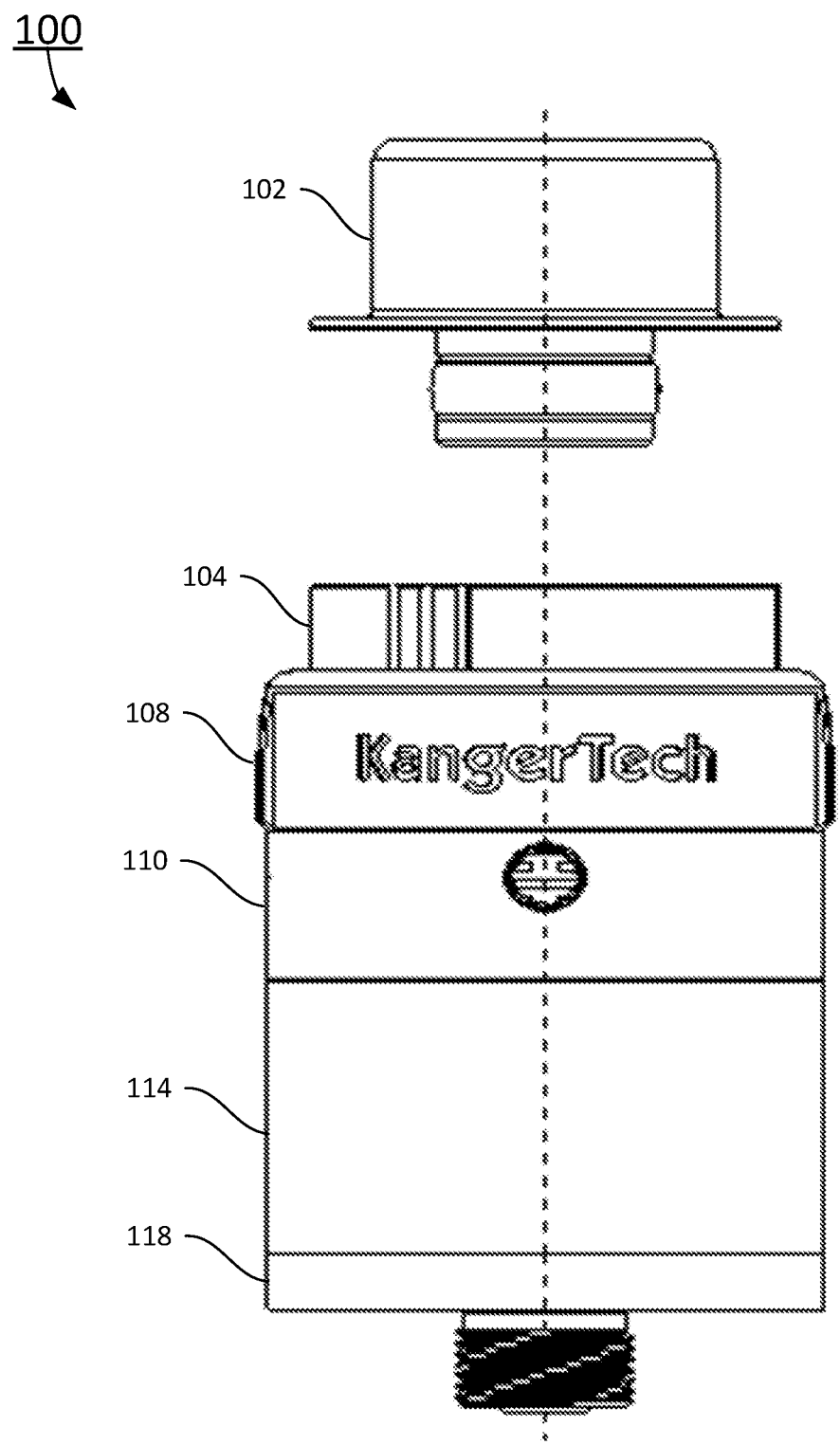
FIG. 5 shows an external view of the electronic cigarette having a mouthpiece removed from a mouthpiece base according to certain embodiments of the present disclosure.

Referring now to FIG. 5, an external view of the exemplary electronic cigarette body 100 having the mouthpiece 102 removed from the mouthpiece base 104 is shown according to certain embodiments of the present disclosure. In certain embodiments, the mouthpiece base 104 defines a center opening to slidedly fit the mouthpiece 102. A sealing ring 1021 of the mouthpiece 102 may be used to ascertain reliable connection between the mouthpiece 102 and the mouthpiece base 104. When removing the mouthpiece 102, the mouthpiece 102 may be pulled upwards to detach the mouthpiece 102 from the mouthpiece base 104 as shown in FIG. 5.

Figure 6:
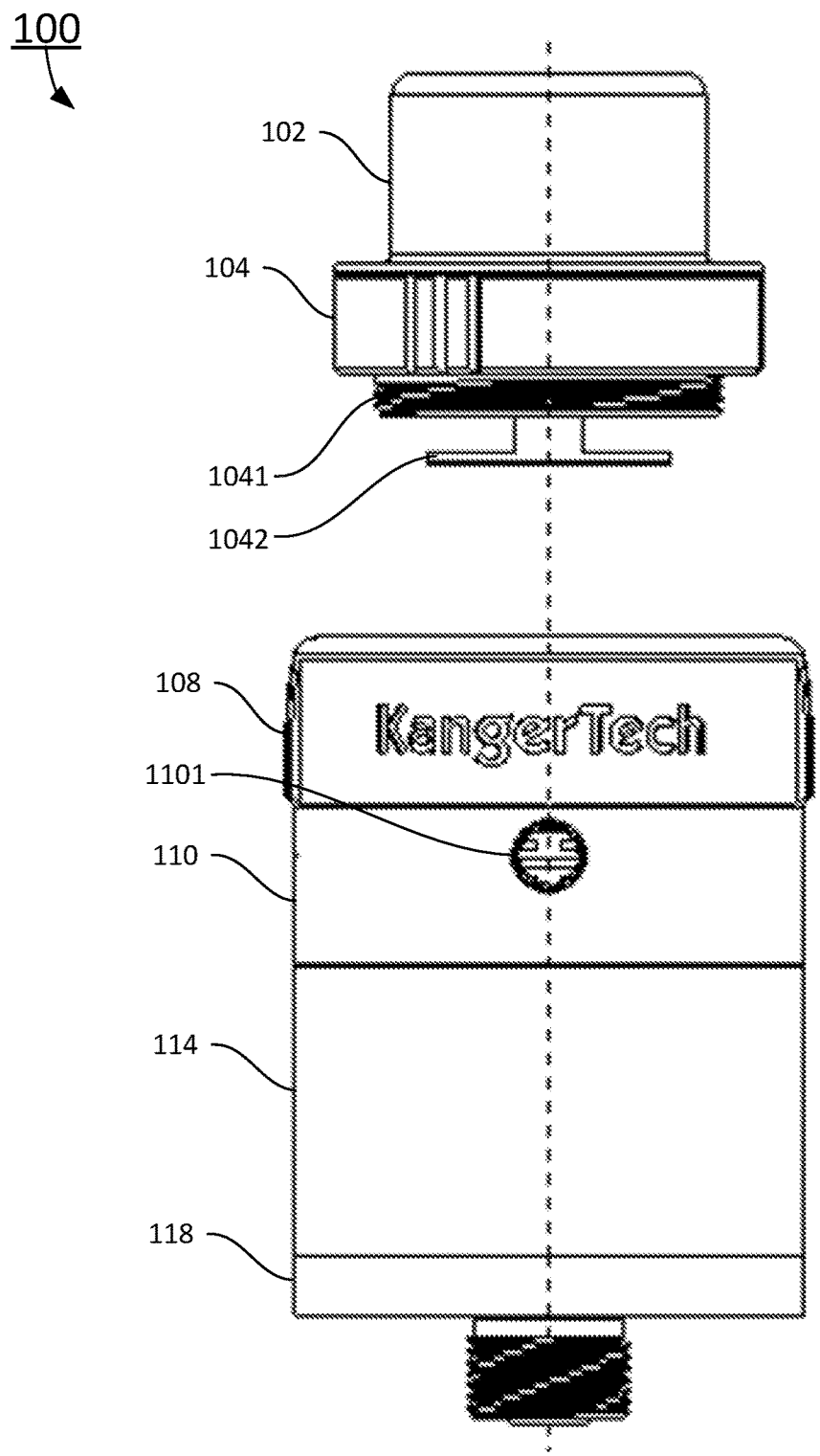
FIG. 6 shows an external view of the electronic cigarette having a mouthpiece and a mouthpiece base removed for replacing the replaceable vaporizer assembly according to certain embodiments of the present disclosure.

Referring now to FIG. 6, an external view of the electronic cigarette having the mouthpiece 102 and the mouthpiece base 104 removed for replacing the replaceable vaporizer assembly 200 according to certain embodiments of the present disclosure. The mouthpiece base 104 may include a negative terminal contact plate 1042. The negative terminal contact plate 1042 of the mouthpiece base 104 is used to press the replaceable vaporizer assembly 200 in place and provide a negative terminal contact to the negative terminal 202 of the replaceable vaporizer assembly 200. When replacing the replaceable vaporizer assembly 200, the mouthpiece 102 and the mouthpiece base 104 may be removed as shown in FIG. 6, by unscrewing the mouthpiece base 104 to detach the external thread 1041 of the mouthpiece base 104 from the internal thread 1081 of the connector base 108.

Figure 7:
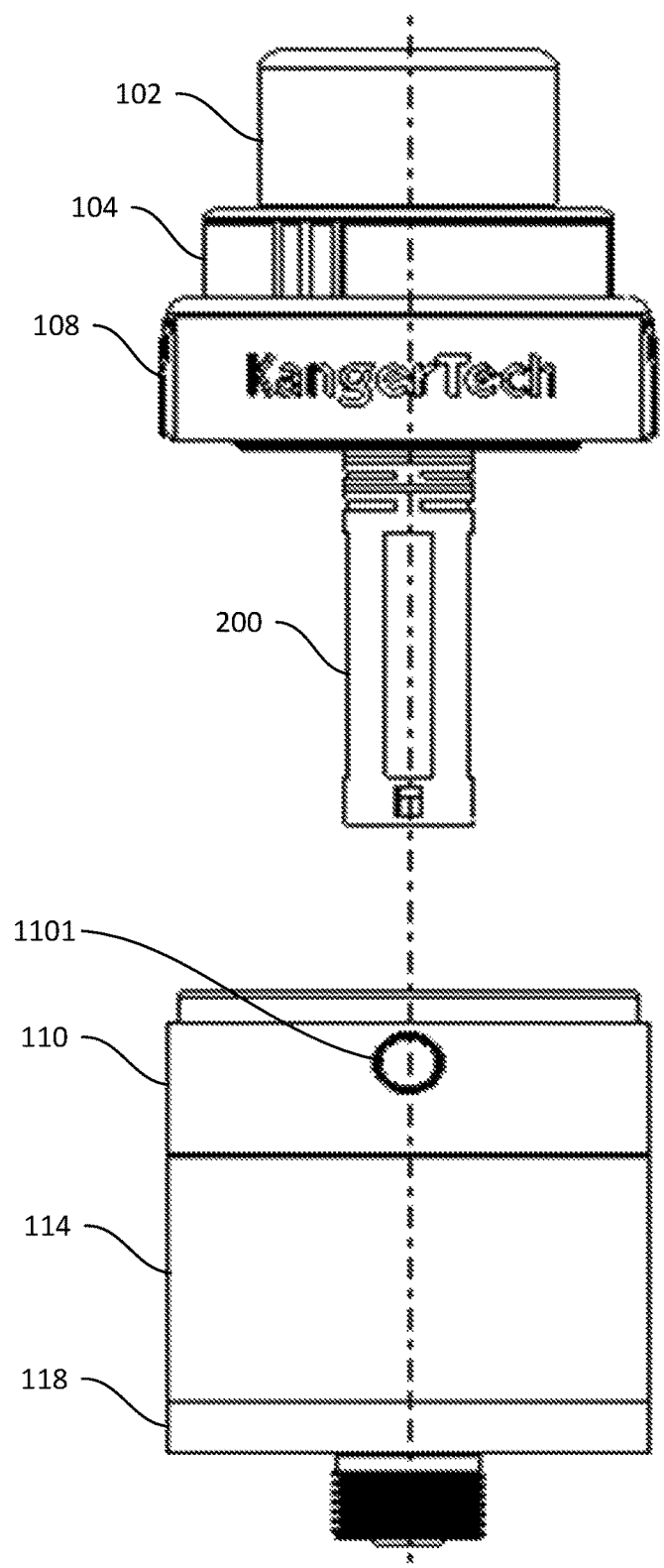
FIG. 7 shows an external view of the electronic cigarette having a mouthpiece, a mouthpiece base, a connector base and a replaceable vaporizer assembly removed for refilling E-liquid according to certain embodiments of the present disclosure.

Referring now to FIG. 7, an external view of the electronic cigarette having a mouthpiece, a mouthpiece base, a connector base and a heating element removed for replacing replaceable vaporizer assembly 200 and/or refill E-liquid into the E-liquid storage tank 114 is shown according to certain embodiments of the present disclosure. When the user wishes to replace the replaceable vaporizer assembly 200, or to refill E-liquid into the E-liquid storage tank 114, the user may unscrewing the connector base 108 to detach the external thread 1082 of the connector base 108 from the first internal thread 1105 of the mounting base 110 and lift the connector base 108 with the mouthpiece 102, the mouthpiece base 104, and the replaceable vaporizer assembly 200 up. With the connector base 108 having the mouthpiece 102, the mouthpiece base 104, and the replaceable vaporizer assembly 200 removed, the electronic cigarette body 100 exposes an opening in the middle of the mounting base 110 for refilling. The combination of connector base 108 having the mouthpiece 102, the mouthpiece base 104, and the replaceable vaporizer assembly 200 may be further disassembled to replace the replaceable vaporizer assembly 200.

Figure 8:
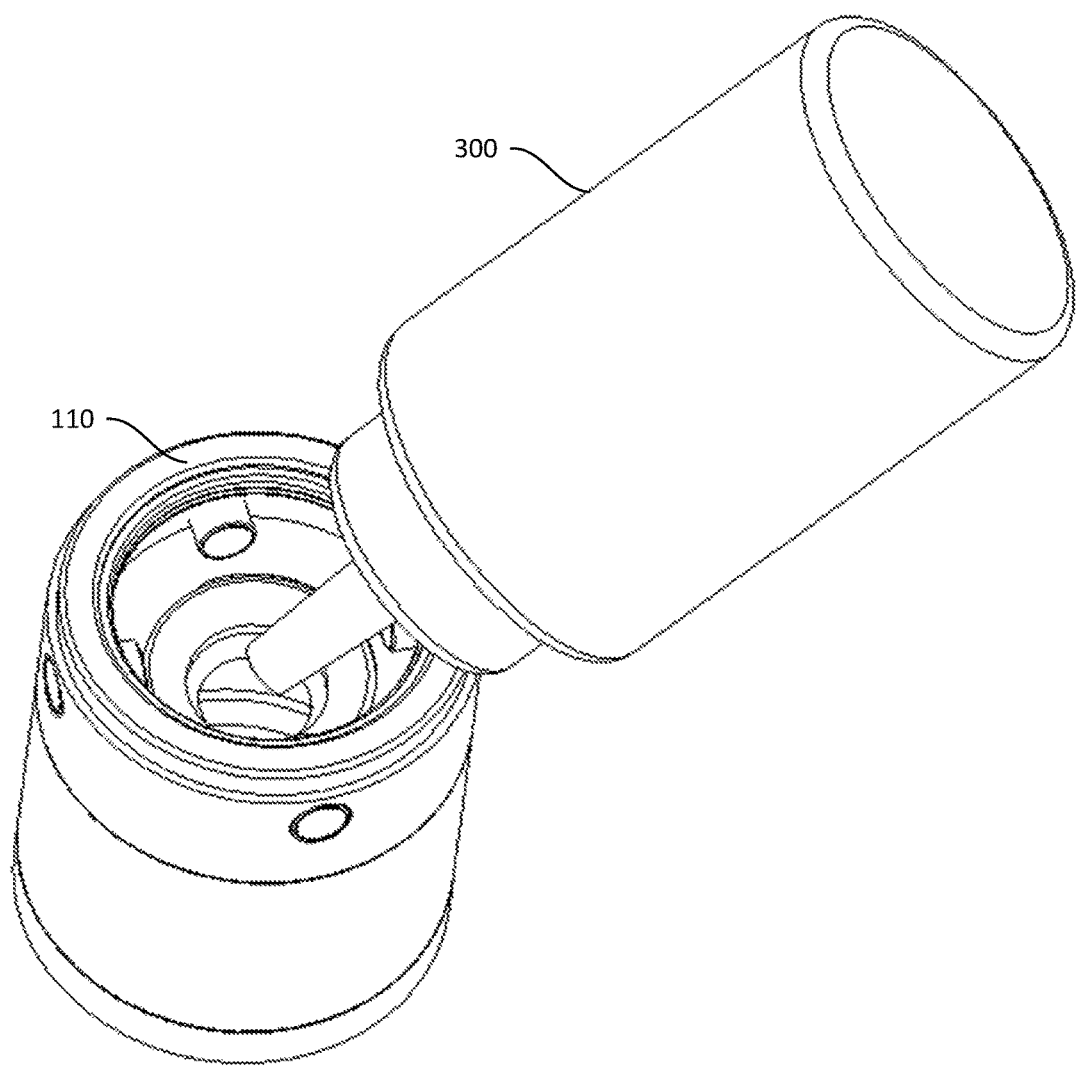
FIG. 8 shows a perspective view of refilling E-liquid into an E-liquid storage tank with a mouthpiece, a mouthpiece base, a connector base and the replaceable vaporizer assembly removed according to certain embodiments of the present disclosure.

Referring now to FIG. 8, a perspective view of refilling E-liquid into an E-liquid storage tank is shown according to certain embodiments of the present disclosure. As shown in FIG. 7, the mouthpiece 102, the mouthpiece base 104, the connector base 108 and the replaceable vaporizer assembly 200 are removed the electronic cigarette body 100, the electronic cigarette body 100 exposes an opening in the middle of the mounting base 110 for refilling E-liquid. In one embodiment, an E-liquid refilling bottle 300 may be used to refill the E-liquid into the E-liquid storage tank 114.

As shown in FIG. 9A, the combination of connector base 108 having the mouthpiece 102, the mouthpiece base 104, and the replaceable vaporizer assembly 200 may be further disassembled to replace the replaceable vaporizer assembly 200.

In certain embodiments, as shown in FIG. 6, the replaceable vaporizer assembly 200 is pressed down by the negative terminal contact plate 1042 of the mouthpiece base 104. Therefore, in order to replace the replaceable vaporizer assembly 200, the user may unscrew the mouthpiece base 104 to detach the external thread 1041 of the mouthpiece base 104 from the internal thread 1081 of the connector base 108 such that the replaceable vaporizer assembly 200 is inside of the connector base 108 without the negative terminal contact plate 1042 of the mouthpiece base 104 holding it down as shown in FIG. 9B. The user may pull the replaceable vaporizer assembly 200 from the top end of the connector base 108 to remove the replaceable vaporizer assembly 200 as shown in FIG. 9C. Once a new replaceable vaporizer assembly 200 is installed inside the connector base 108, the user may install the mouthpiece base 104 and the mouthpiece 102 back in place.

Figures 10A, 10B:
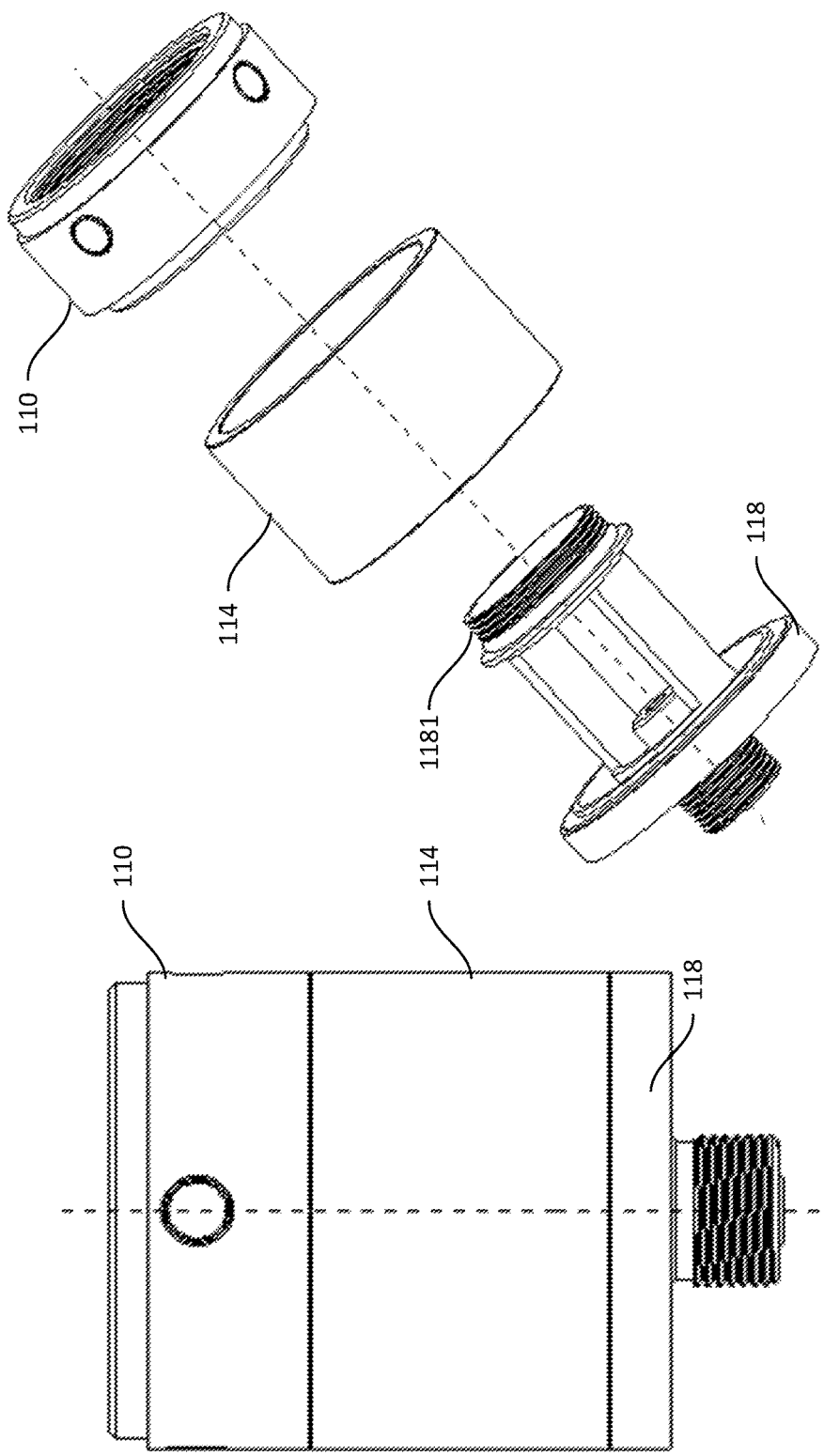
FIG. 10A shows an external view of an E-liquid storage tank.
FIG. 10B shows an exploded perspective view of the E-liquid storage tank according to certain embodiments of the present disclosure.

FIG. 10A shows an external view of an E-liquid storage tank, and FIG. 10B shows an exploded perspective view of the E-liquid storage tank according to certain embodiments of the present disclosure. In certain embodiments, the E-liquid storage tank 114 is positioned between the mounting base 110 and the connector 118. The E-liquid storage tank 114 is sealed by a first sealing ring 112 between the mounting base 110 on a top end of the E-liquid storage tank 114 and a second sealing ring 116 between a bottom end of the E-liquid storage tank 114 and the connector 118. E-liquid in the E-liquid storage tank 114 is in communication with the E-liquid storage medium.

In certain embodiments, the E-liquid storage tank 114 may be replaced. When the user wishes to replace the E-liquid storage tank 114, the user may unscrew the mounting base 110 to detach the second internal thread 1106 of the mounting base 110 from the first external thread 1181 of the connector 118. The E-liquid storage tank 114 may be replaced as shown in FIG. 10B.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims, the foregoing description and the exemplary embodiments described therein, and accompanying drawings.

What is claimed is:

1. A replaceable vaporizer assembly, comprising:
a tube-shaped E-liquid storage medium for receiving and storing E-liquid from an E-liquid storage tank, wherein a hollow cavity of the tube-shaped E-liquid storage medium forms an E-liquid vapor passage; and
a tube-shaped heating element, coaxially positioned outside of the tube-shaped E-liquid storage medium for heating the E-liquid stored in the E-liquid storage medium, wherein the heating element comprises a positive terminal electrically coupled to a positive terminal of a power module, and a negative terminal electrically coupled to a negative terminal of the power module, when the power module is switched on the heating element is energized by the power module to heat E-liquid stored in the E-liquid storage medium to produce E-liquid vapor for an electronic cigarette.

2. The replaceable vaporizer assembly of claim 1, wherein the tube-shaped E-liquid storage medium comprises:
a tube-shaped E-liquid storage medium having the heating element wound on an exterior surface of the tube-shaped E-liquid storage medium, or
a tube-shaped E-liquid storage medium having the heating element wound on an interior surface of the tube-shaped E-liquid storage medium, wherein the tube-shaped E-liquid storage medium comprises:
cotton fibers;
polypropylene fibers;
terylene fibers;
nylon fibers;
porous ceramic materials; and
any combination thereof.

3. The replaceable vaporizer assembly of claim 1, wherein the heating element is made of resistive electrical conductive materials having large contact area with the E-liquid storage medium to increase amount of E-liquid vapor generated.

4. The replaceable vaporizer assembly of claim 1, wherein the heating element comprises:
a grid shaped heating element;
a mesh shaped heating element;
a net shaped heating element;
a spiral heating element; and
any combination thereof.

5. The replaceable vaporizer assembly of claim 1, wherein the heating element is formed on a cylindrical tube having a top portion, a middle portion and a bottom portion, and wherein the heating element may be formed at the top portion, the middle portion, or the bottom portion of the cylindrical tube.

6. The replaceable vaporizer assembly of claim 5, wherein the heating element comprises a plurality of heating elements, wherein the plurality of heating elements are electrically coupled in serial to increase amount of E-liquid vapor generated; and wherein the plurality of heating elements may be formed at the top portion, the middle portion, and/or the bottom portion of the cylindrical tube.

7. An electronic cigarette body comprising:
a mouthpiece base defining a center opening, wherein the mouthpiece base comprises an external thread;
a mouthpiece configured to slidedly fit into the center opening of the mouthpiece base;
a connector base having an internal thread configured to threadedly connect to the external thread of the mouthpiece base, and an external thread;
a mounting base defining a plurality of air intake openings, wherein the mounting base comprises a first internal thread configured to threadedly connect to the external thread of the connector base, and a second internal thread;
an E-liquid storage tank having a top end and a bottom end; and
a connector having a first external thread configured to threadedly connect to the second internal thread of the mounting base, and a second external thread configured to threadedly connect to a negative terminal of a power module.

8. The electronic cigarette body of claim 7, further comprising a replaceable vaporizer assembly, wherein the replaceable vaporizer assembly comprises:
an E-liquid storage medium; and
a heating element having a positive terminal, and a negative terminal, wherein the positive terminal is electrically coupled to a positive terminal of the power module, and the negative terminal is electrically coupled to a negative terminal of the power module, when the power module is switched on the heating element is energized by the power module to heat E-liquid stored in the E-liquid storage medium from the E-liquid storage tank to produce E-liquid vapor for an electronic cigarette.

9. The electronic cigarette body of claim 8, further comprising:
a positive terminal of the replaceable vaporizer assembly configured to electrically coupled to the positive terminal of the heating element, and the positive terminal of the power module; and
an insulation tube configured to insulate the positive terminal of the replaceable vaporizer assembly and the second external thread of the connector, wherein the second external thread of the connector forms a negative terminal of the replaceable vaporizer assembly.

10. The electronic cigarette body of claim 8, wherein the E-liquid storage tank is positioned between the mounting base and the connector, sealed by a first sealing ring between the mounting base on the top end of the E-liquid storage tank and a second sealing ring between the bottom end of the E-liquid storage tank and the connector, and wherein the E-liquid in the E-liquid storage tank is in communication with the E-liquid storage medium.

11. The electronic cigarette body of claim 8, wherein the mounting base and the connector base are threadedly connected through the first internal thread of the mounting base and the external thread of the connector base to form an air chamber inside of the mounting base and the connector base, wherein outside air enters the air chamber through the plurality of air intake openings, is vaporized by the replaceable vaporizer assembly, goes up through a plurality of gaps between the mounting base and the connector base, and exits the electronic cigarette body through the mouthpiece.

12. An electronic cigarette comprising:
an electronic cigarette body having a mouthpiece installed in a mouthpiece base, a connector base, a mounting base defining a plurality of air intake openings, an E-liquid storage tank, and a connector; and
a replaceable vaporizer assembly, wherein the mounting base and the connector base are threadedly connected through a first internal thread of the mounting base and an external thread of the connector base to form an air chamber inside of the mounting base and the connector base, wherein outside air enters the air chamber to be vaporized by the replaceable vaporizer assembly through the plurality of air intake openings, goes up through a plurality of gaps between the mounting base and the connector base, and exits the electronic cigarette body through the mouthpiece, wherein the connector base comprises an internal thread configured to threadedly connect to an external thread of the mouthpiece base, and the external thread, wherein the mounting base comprises the first internal thread configured to threadedly connect to the external thread of the connector base, and a second internal thread, and wherein the connector comprises a first external thread configured to threadedly connect to the second internal thread of the mounting base, and a second external thread configured to threadedly connect to a negative terminal of a power module.

13. The electronic cigarette of claim 12, wherein the electronic cigarette body further comprises:
   a positive terminal of the electronic cigarette body configured to electrically coupled to the positive terminal of a heating element, and the positive terminal of the power module; and
   an insulation tube configured to insulate the positive terminal of the electronic cigarette body and the second external thread of the connector, wherein the second external thread of the connector forms a negative terminal of the electronic cigarette body.

14. The electronic cigarette of claim 12, wherein the E-liquid storage tank is positioned between the mounting base and the connector, sealed by a first sealing ring between the mounting base on the top end of the E-liquid storage tank and a second sealing ring between the bottom end of the E-liquid storage tank and the connector, and wherein the E-liquid in the E-liquid storage tank is in communication with the E-liquid storage medium.

15. The electronic cigarette of claim 12, wherein the replaceable vaporizer assembly comprises:
   an E-liquid storage medium; and
   the heating element having the positive terminal, and the negative terminal, wherein the positive terminal is electrically coupled to a positive terminal of the power module, and the negative terminal is electrically coupled to a negative terminal of the power module, when the power module is switched on the heating element is energized by the power module to heat E-liquid stored in the E-liquid storage medium from the E-liquid storage tank to produce E-liquid vapor for the electronic cigarette.

16. The electronic cigarette of claim 15, wherein the tube-shaped E-liquid storage medium comprises:
   a tube-shaped E-liquid storage medium having the heating element wound on an exterior surface of the tube-shaped E-liquid storage medium, or
   a tube-shaped E-liquid storage medium having the heating element wound on an interior surface of the tube-shaped E-liquid storage medium, wherein the tube-shaped E-liquid storage medium comprises:
   cotton fibers;
   polypropylene fibers;
   terylene fibers;
   nylon fibers;
   porous ceramic materials; and
   any combination thereof.

17. The electronic cigarette of claim 15, wherein the heating element comprises a plurality of heating elements, wherein the plurality of heating elements are electrically coupled in serial to increase amount of E-liquid vapor generated.

18. The electronic cigarette of claim 15, wherein the heating element is made of resistive electrical conductive materials having large contact area with the E-liquid storage medium to increase amount of E-liquid vapor generated.

19. The electronic cigarette of claim 15, wherein the heating element comprises:
   a grid shaped heating element;
   a mesh shaped heating element;
   a net shaped heating element;
   a spiral heating element; and
   any combination thereof.

* * * * *